(12) United States Patent
Onuoha et al.

(10) Patent No.: US 11,180,553 B2
(45) Date of Patent: Nov. 23, 2021

(54) CHIMERIC ANTIGEN RECEPTOR

(71) Applicant: AUTOLUS LIMITED, London (GB)

(72) Inventors: Shimobi Onuoha, London (GB); Martin Pulé, London (GB); Simon Thomas, London (GB); Shaun Cordoba, London (GB); Evangelia Kokalaki, London (GB)

(73) Assignee: AUTOLUS LIMITED, London (GB)

( * ) Notice: Subject to any disclaimer, the term of this patent is extended or adjusted under 35 U.S.C. 154(b) by 319 days.

(21) Appl. No.: 16/310,121

(22) PCT Filed: Jun. 15, 2017

(86) PCT No.: PCT/GB2017/051742
§ 371 (c)(1),
(2) Date: Dec. 14, 2018

(87) PCT Pub. No.: WO2017/216561
PCT Pub. Date: Dec. 21, 2017

(65) Prior Publication Data
US 2019/0177412 A1  Jun. 13, 2019

(30) Foreign Application Priority Data
Jun. 16, 2016 (GB) .................................... 1610512

(51) Int. Cl.
| | | |
|---|---|---|
| *C07K 16/28* | (2006.01) | |
| *C07K 14/725* | (2006.01) | |
| *A61P 35/02* | (2006.01) | |
| *A61P 35/00* | (2006.01) | |
| *A61K 35/17* | (2015.01) | |
| *C07K 14/705* | (2006.01) | |
| *A61K 38/00* | (2006.01) | |

(52) U.S. Cl.
CPC .......... *C07K 16/2803* (2013.01); *A61K 35/17* (2013.01); *A61P 35/00* (2018.01); *A61P 35/02* (2018.01); *C07K 14/7051* (2013.01); *C07K 14/70517* (2013.01); *C07K 14/70578* (2013.01); *A61K 38/00* (2013.01); *C07K 2317/52* (2013.01); *C07K 2317/53* (2013.01); *C07K 2317/565* (2013.01); *C07K 2317/622* (2013.01); *C07K 2317/73* (2013.01); *C07K 2317/76* (2013.01); *C07K 2319/03* (2013.01); *C07K 2319/30* (2013.01); *C07K 2319/33* (2013.01)

(58) Field of Classification Search
CPC .......... C07K 16/2803; C07K 14/70517; C07K 14/70578; C07K 14/7051; C07K 2317/52; C07K 2317/53; C07K 2317/565; C07K 2319/30; A61P 35/02; A61P 35/00; A61K 35/17; A61K 38/00
See application file for complete search history.

(56) References Cited

U.S. PATENT DOCUMENTS

| | | |
|---|---|---|
| 7,052,906 B1 | 5/2006 | Lawson et al. |
| 2004/0192900 A1 | 9/2004 | Kunz et al. |
| 2007/0264257 A1* | 11/2007 | Dunussi-Joannopoulos ................ C07K 16/2803 424/132.1 |
| 2011/0027273 A1 | 2/2011 | Dunussi-Joannopoulos et al. |
| 2014/0274909 A1* | 9/2014 | Orentas ................ C07K 14/705 514/19.3 |
| 2016/0015831 A1 | 1/2016 | Lin et al. |
| 2016/0333114 A1* | 11/2016 | Williams ......... C07K 14/70521 |
| 2017/0340704 A1 | 11/2017 | Pule et al. |
| 2017/0340705 A1 | 11/2017 | Pule et al. |
| 2017/0369550 A1 | 12/2017 | Pule et al. |
| 2018/0050065 A1 | 2/2018 | Pule et al. |
| 2018/0371054 A1 | 12/2018 | Pule et al. |

FOREIGN PATENT DOCUMENTS

| | | |
|---|---|---|
| WO | WO-93/11237 A1 | 6/1993 |
| WO | WO-2000/063372 A1 | 10/2000 |
| WO | WO-03/093320 A2 | 11/2003 |
| WO | WO-2006/042240 A2 | 4/2006 |
| WO | WO-2013/153391 A1 | 10/2013 |
| WO | WO-2015/196089 A1 | 12/2015 |

(Continued)

OTHER PUBLICATIONS

Gerdes et al. Emerging understanding of multiscale tumor heterogeneity. Frontiers In Oncology. Dec. 2014 | vol. 4 | Article 366 (Year: 2014).*
Srivastava et al. Engineering CAR-T cells: Design concepts.Trends in Immunology, Aug. 2015, vol. 36, No. 8 (Year: 2015).*
Sadelain et al., "The Basic Principles of Chimeric Antigen Receptor Design," Cancer Discovery 3:388-398 (2013).
Campana et al., Immunophenotyping of leukemia, J. Immunol. Methods, 243(1-2):59-75 (2000).
Choudhuri et al., T-cell receptor triggering is critically dependent on the dimensions of its peptide-MHC ligand, Nature 436:578-582 (2005).

(Continued)

*Primary Examiner* — Daniel E Kolker
*Assistant Examiner* — Brian Hartnett
(74) *Attorney, Agent, or Firm* — Marshall, Gerstein & Borun LLP

(57) ABSTRACT

The present invention provides a chimeric antigen receptor (CAR) which binds human CD22, having an antigen-binding domain which comprises a) a heavy chain variable region (VH) having complementarity determining regions (CDRs) with the following sequences: CDR1—NYWIH (SEQ ID No. 1); CDR2—GINPGNNYATYRRKFQG (SEQ ID No. 2) CDR3—EGYGNYGAWFAY (SEQ ID No. 3); and b) a light chain variable region (VL) having CDRs with the following sequences: CDR1—RSSQSLANSYGNTFLS (SEQ ID No. 4); CDR2—GISNRFS (SEQ ID No. 5) CDR3—LQGTHQPYT (SEQ ID No. 6). The present invention also provides a cell comprising such a CAR and the use of such a cell to treat cancer.

12 Claims, 5 Drawing Sheets
Specification includes a Sequence Listing.

(56) References Cited

FOREIGN PATENT DOCUMENTS

WO     WO-2016/014576 A1     1/2016

OTHER PUBLICATIONS

Davis et al., The kinetic-segregation model: TCR triggering and beyond, Nat Immunol., 7(8):803-9 (2006).

Donnelly et al., The 'cleavage' activities of foot-and-mouth disease virus 2A site-directed mutants and naturally occurring '2A-like' sequences. *J. Gen. Virol.* 82: 1027-41 (2001).

Haso et al., Anti-CD22-chimeric antigen receptors targeting B-cell precursor acute lymphoblastic leukemia, Blood, 121(7):1165-74 (2013).

Hombach et al., T cell activation by antibody-like immunoreceptors: the position of the binding epitope within the target molecule determines the efficiency of activation of redirected T cells, J. Immunol., 178(7):4650-7 (2007).

International Preliminary Report on Patentability for Application No. PCT/GB2017/051742, dated Dec. 18, 2018.

International Search Report and Written Opinion for Application No. PCT/GB2017/051742, dated Aug. 25, 2017.

James et al., Antigen sensitivity of CD22-specific chimeric TCR is modulated by target epitope distance from the cell membrane, J. Immunol., 180(10):7028-38 (2008).

Liu et al., A seven-helix coiled coil. *Proc. Natl. Acad. Sci. USA*, 103: 15457-62 (2006).

Long et al., Lessons learned from a highly-active CD22-specific chimeric antigen receptor, Oncoimmunology, 2(4):e23621 (2013).

Lupas et al., The structure of alpha-helical coiled coils. *Adv. Protein Chem.* 70: 37-8 (2007).

Mahrenholz et al., Complex networks govern coiled-coil oligomerization—predicting and profiling by means of a machine learning approach. *Mol. Cell. Proteomics*, 10(5): M110.004994 (2011).

Orentas et al., 325. Targeting B Cell Precursor Acute Lymphoblastic Leukemia (ALL) with Chimeric Antigen Receptors (CARs) Specific for CD19 or CD22, Molecular Therapy, 21:S125 (2013).

Zaccai et al., A de novo peptide hexamer with a mutable channel. *Nat. Chem. Biol.* 7: 935-41 (2011).

U.S. Appl. No. 15/529,690 (US-2017-0369550), filed May 25, 2017.

U.S. Appl. No. 15/631,948 (US-2017-0340704), filed Jun. 23, 2017.

U.S. Appl. No. 16/024,445 (US-2018-0371054), filed Jun. 29, 2018.

U.S. Appl. No. 15/632,119 (US-2017-0340705), filed Jun. 23, 2017.

U.S. Appl. No. 16/211,538, filed Dec. 6, 2018.

U.S. Appl. No. 15/560,558 (US-2018-0050065), filed Sep. 22, 2017.

\* cited by examiner

SEQUENCE LISTING

```
<160> NUMBER OF SEQ ID NOS: 36

<210> SEQ ID NO 1
<211> LENGTH: 5
<212> TYPE: PRT
<213> ORGANISM: Artificial Sequence
<220> FEATURE:
<223> OTHER INFORMATION: heavy chain variable region (VH)
      complementarity determining region (CDR) CDR1

<400> SEQUENCE: 1

Asn Tyr Trp Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: heavy chain variable region (VH) CDR2

<400> SEQUENCE: 2

Gly Ile Asn Pro Gly Asn Asn Tyr Ala Thr Tyr Arg Arg Lys Phe Gln
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: heavy chain variable region (VH) CDR3

<400> SEQUENCE: 3

Glu Gly Tyr Gly Asn Tyr Gly Ala Trp Phe Ala Tyr
1               5                   10

<210> SEQ ID NO 4
```

<211> LENGTH: 16
<212> TYPE: PRT
<213> ORGANISM: Artificial Sequence
<220> FEATURE:
<223> OTHER INFORMATION: light chain variable region (VL) CDR1

<400> SEQUENCE: 4

Arg Ser Ser Gln Ser Leu Ala Asn Ser Tyr Gly Asn Thr Phe Leu Ser
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: light chain variable region (VL) CDR2

<400> SEQUENCE: 5

Gly Ile Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: light chain variable region (VL) CDR3

<400> SEQUENCE: 6

Leu Gln Gly Thr His Gln Pro Tyr Thr
1               5

<210> SEQ ID NO 7
<211> LENGTH: 121
<212> TYPE: PRT
<213> ORGANISM: Artificial Sequence
<220> FEATURE:
<223> OTHER INFORMATION: VH sequence from Inotuzumab

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asn Tyr
            20                  25                  30

Trp Ile His Trp Val Arg Gln Ala Pro Gly Gln Gly Leu Glu Trp Ile
        35                  40                  45

Gly Gly Ile Asn Pro Gly Asn Asn Tyr Ala Thr Tyr Arg Arg Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser
        115                 120

<210> SEQ ID NO 8
<211> LENGTH: 112
<212> TYPE: PRT
<213> ORGANISM: Artificial Sequence
<220> FEATURE:
<223> OTHER INFORMATION: VL sequence from Inotuzumab

<400> SEQUENCE: 8

Asp Val Gln Val Thr Gln Ser Pro Ser Leu Ser Ala Ser Val Gly
1               5                   10                  15

Asp Arg Val Thr Ile Thr Cys Arg Ser Ser Gln Ser Leu Ala Asn Ser
            20                  25                  30

Tyr Gly Asn Thr Phe Leu Ser Trp Tyr Leu His Lys Pro Gly Lys Ala
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Gln Pro Tyr Thr Phe Gly Gln Gly Thr Lys Val Glu Ile Lys
            100                 105                 110

<210> SEQ ID NO 9
<211> LENGTH: 21
<212> TYPE: PRT
<213> ORGANISM: Artificial Sequence
<220> FEATURE:
<223> OTHER INFORMATION: signal peptide

<400> SEQUENCE: 9

Met Gly Thr Ser Leu Leu Cys Trp Met Ala Leu Cys Leu Leu Gly Ala
1               5                   10                  15

Asp His Ala Asp Gly
            20

<210> SEQ ID NO 10
<211> LENGTH: 21
<212> TYPE: PRT
<213> ORGANISM: Artificial Sequence
<220> FEATURE:
<223> OTHER INFORMATION: signal peptide derived from IgG1

<400> SEQUENCE: 10

Met Ser Leu Pro Val Thr Ala Leu Leu Leu Pro Leu Ala Leu Leu Leu
1               5                   10                  15

His Ala Ala Arg Pro
            20

<210> SEQ ID NO 11
<211> LENGTH: 20
<212> TYPE: PRT
<213> ORGANISM: Artificial Sequence
<220> FEATURE:
<223> OTHER INFORMATION: signal peptide derived from CD8

<400> SEQUENCE: 11

Met Ala Val Pro Thr Gln Val Leu Gly Leu Leu Leu Leu Trp Leu Thr
1               5                   10                  15

Asp Ala Arg Cys
            20

<210> SEQ ID NO 12
<211> LENGTH: 234
<212> TYPE: PRT
<213> ORGANISM: Artificial Sequence
<220> FEATURE:
<223> OTHER INFORMATION: spacer sequence, hinge-CH2CH3 of human IgG1

<400> SEQUENCE: 12

```
Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230
```

<210> SEQ ID NO 13
<211> LENGTH: 46
<212> TYPE: PRT
<213> ORGANISM: Artificial Sequence
<220> FEATURE:
<223> OTHER INFORMATION: spacer sequence, human CD8 stalk

<400> SEQUENCE: 13

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45
```

<210> SEQ ID NO 14
<211> LENGTH: 20
<212> TYPE: PRT
<213> ORGANISM: Artificial Sequence
<220> FEATURE:
<223> OTHER INFORMATION: spacer sequence, human IgG1 hinge

<400> SEQUENCE: 14

```
Ala Glu Pro Lys Ser Pro Asp Lys Thr His Thr Cys Pro Pro Cys Pro
1               5                   10                  15
```

<210> SEQ ID NO 15
<211> LENGTH: 57
<212> TYPE: PRT
<213> ORGANISM: Artificial Sequence
<220> FEATURE:
<223> OTHER INFORMATION: sequence of coiled coil domain (Kinesin motor protein: parallel homodimer)

<400> SEQUENCE: 15

```
Met His Ala Ala Leu Ser Thr Glu Val Val His Leu Arg Gln Arg Thr
1               5                   10                  15
Glu Glu Leu Leu Arg Cys Asn Glu Gln Gln Ala Ala Glu Leu Glu Thr
            20                  25                  30
Cys Lys Glu Gln Leu Phe Gln Ser Asn Met Glu Arg Lys Glu Leu His
        35                  40                  45
Asn Thr Val Met Asp Leu Arg Gly Asn
    50                  55
```

<210> SEQ ID NO 16
<211> LENGTH: 50
<212> TYPE: PRT
<213> ORGANISM: Artificial Sequence
<220> FEATURE:
<223> OTHER INFORMATION: sequence of coiled coil domain (Hepatitis D delta antigen: parallel homodimer)

<400> SEQUENCE: 16

```
Gly Arg Glu Asp Ile Leu Glu Gln Trp Val Ser Gly Arg Lys Lys Leu
1               5                   10                  15
Glu Glu Leu Glu Arg Asp Leu Arg Lys Leu Lys Lys Lys Ile Lys Lys
            20                  25                  30
Leu Glu Glu Asp Asn Pro Trp Leu Gly Asn Ile Lys Gly Ile Ile Gly
        35                  40                  45
Lys Tyr
    50
```

<210> SEQ ID NO 17
<211> LENGTH: 61
<212> TYPE: PRT
<213> ORGANISM: Artificial Sequence
<220> FEATURE:
<223> OTHER INFORMATION: sequence of coiled coil domain (Archaeal box C/D sRNP core protein: anti-parallel heterodimer)

<400> SEQUENCE: 17

```
Arg Tyr Val Val Ala Leu Val Lys Ala Leu Glu Glu Ile Asp Glu Ser
1               5                   10                  15
Ile Asn Met Leu Asn Glu Lys Leu Glu Asp Ile Arg Ala Val Lys Glu
            20                  25                  30
Ser Glu Ile Thr Glu Lys Phe Glu Lys Lys Ile Arg Glu Leu Arg Glu
        35                  40                  45
Leu Arg Arg Asp Val Glu Arg Glu Ile Glu Glu Val Met
    50                  55                  60
```

<210> SEQ ID NO 18
<211> LENGTH: 31
<212> TYPE: PRT
<213> ORGANISM: Artificial Sequence
<220> FEATURE:
<223> OTHER INFORMATION: sequence of coiled coil domain (Mannose-binding protein A: parallel homotrimer)

<400> SEQUENCE: 18

Ala Ile Glu Val Lys Leu Ala Asn Met Glu Ala Ile Asn Thr Leu
1               5                   10                  15

Lys Ser Lys Leu Glu Leu Thr Asn Lys Leu His Ala Phe Ser Met
            20                  25                  30

<210> SEQ ID NO 19
<211> LENGTH: 29
<212> TYPE: PRT
<213> ORGANISM: Artificial Sequence
<220> FEATURE:
<223> OTHER INFORMATION: sequence of coiled coil domain (Coiled-coil
      serine-rich protein 1: parallel homotrimer)

<400> SEQUENCE: 19

Glu Trp Glu Ala Leu Glu Lys Lys Leu Ala Ala Leu Glu Ser Lys Leu
1               5                   10                  15

Gln Ala Leu Glu Lys Lys Leu Glu Ala Leu Glu His Gly
            20                  25

<210> SEQ ID NO 20
<211> LENGTH: 24
<212> TYPE: PRT
<213> ORGANISM: Artificial Sequence
<220> FEATURE:
<223> OTHER INFORMATION: sequence of coiled coil domain (Polypeptide
      release factor 2: anti-parallel heterotrimer Chain A)

<400> SEQUENCE: 20

Ile Asn Pro Val Asn Asn Arg Ile Gln Asp Leu Thr Glu Arg Ser Asp
1               5                   10                  15

Val Leu Arg Gly Tyr Leu Asp Tyr
            20

<210> SEQ ID NO 21
<211> LENGTH: 51
<212> TYPE: PRT
<213> ORGANISM: Artificial Sequence
<220> FEATURE:
<223> OTHER INFORMATION: sequence of coiled coil domain (Polypeptide
      release factor 2: anti-parallel heterotrimer Chain B)

<400> SEQUENCE: 21

Val Val Asp Thr Leu Asp Gln Met Lys Gln Gly Leu Glu Asp Val Ser
1               5                   10                  15

Gly Leu Leu Glu Leu Ala Val Glu Ala Asp Asp Glu Thr Phe Asn
            20                  25                  30

Glu Ala Val Ala Glu Leu Asp Ala Leu Glu Glu Lys Leu Ala Gln Leu
        35                  40                  45

Glu Phe Arg
    50

<210> SEQ ID NO 22
<211> LENGTH: 51
<212> TYPE: PRT
<213> ORGANISM: Artificial Sequence
<220> FEATURE:
<223> OTHER INFORMATION: sequence of coiled coil domain (SNAP-25 and
      SNARE: parallel heterotetramer Chain A)

<400> SEQUENCE: 22

Ile Glu Thr Arg His Ser Glu Ile Ile Lys Leu Glu Asn Ser Ile Arg

```
                1               5                  10                  15
            Glu Leu His Asp Met Phe Met Asp Met Ala Met Leu Val Glu Ser Gln
                            20                  25                  30
            Gly Glu Met Ile Asp Arg Ile Glu Tyr Asn Val Glu His Ala Val Asp
                    35                  40                  45
            Tyr Val Glu
                    50

<210> SEQ ID NO 23
<211> LENGTH: 67
<212> TYPE: PRT
<213> ORGANISM: Artificial Sequence
<220> FEATURE:
<223> OTHER INFORMATION: sequence of coiled coil domain (SNAP-25 and
      SNARE: parallel heterotetramer Chain B)

<400> SEQUENCE: 23

Ala Leu Ser Glu Ile Glu Thr Arg His Ser Glu Ile Ile Lys Leu Glu
            1               5                   10                  15
            Asn Ser Ile Arg Glu Leu His Asp Met Phe Met Asp Met Ala Met Leu
                            20                  25                  30
            Val Glu Ser Gln Gly Glu Met Ile Asp Arg Ile Glu Tyr Asn Val Glu
                    35                  40                  45
            His Ala Val Asp Tyr Val Glu Arg Ala Val Ser Asp Thr Lys Lys Ala
                    50                  55                  60
            Val Lys Tyr
            65

<210> SEQ ID NO 24
<211> LENGTH: 69
<212> TYPE: PRT
<213> ORGANISM: Artificial Sequence
<220> FEATURE:
<223> OTHER INFORMATION: sequence of coiled coil domain (SNAP-25 and
      SNARE: parallel heterotetramer Chain C)

<400> SEQUENCE: 24

Glu Leu Glu Glu Met Gln Arg Arg Ala Asp Gln Leu Ala Asp Glu Ser
            1               5                   10                  15
            Leu Glu Ser Thr Arg Arg Met Leu Gln Leu Val Glu Glu Ser Lys Asp
                            20                  25                  30
            Ala Gly Ile Arg Thr Leu Val Met Leu Asp Glu Gln Gly Glu Gln Leu
                    35                  40                  45
            Glu Arg Ile Glu Glu Gly Met Asp Gln Ile Asn Lys Asp Met Lys Glu
                    50                  55                  60
            Ala Glu Lys Asn Leu
            65

<210> SEQ ID NO 25
<211> LENGTH: 51
<212> TYPE: PRT
<213> ORGANISM: Artificial Sequence
<220> FEATURE:
<223> OTHER INFORMATION: sequence of coiled coil domain (SNAP-25 and
      SNARE: parallel heterotetramer Chain D)

<400> SEQUENCE: 25

Ile Glu Thr Arg His Ser Glu Ile Ile Lys Leu Glu Asn Ser Ile Arg
            1               5                   10                  15
            Glu Leu His Asp Met Phe Met Asp Met Ala Met Leu Val Glu Ser Gln
                            20                  25                  30
```

```
Gly Glu Met Ile Asp Arg Ile Glu Tyr Asn Val Glu His Ala Val Asp
            35                  40                  45

Tyr Val Glu
    50

<210> SEQ ID NO 26
<211> LENGTH: 20
<212> TYPE: PRT
<213> ORGANISM: Artificial Sequence
<220> FEATURE:
<223> OTHER INFORMATION: sequence of coiled coil domain (Lac repressor:
      parallel homotetramer)

<400> SEQUENCE: 26

Ser Pro Arg Ala Leu Ala Asp Ser Leu Met Gln Leu Ala Arg Gln Val
1               5                   10                  15

Ser Arg Leu Glu
            20

<210> SEQ ID NO 27
<211> LENGTH: 136
<212> TYPE: PRT
<213> ORGANISM: Artificial Sequence
<220> FEATURE:
<223> OTHER INFORMATION: sequence of coiled coil domain (Apolipoprotein
      E: anti-parallel heterotetramer)

<400> SEQUENCE: 27

Ser Gly Gln Arg Trp Glu Leu Ala Leu Gly Arg Phe Trp Asp Tyr Leu
1               5                   10                  15

Arg Trp Val Gln Thr Leu Ser Glu Gln Val Gln Glu Glu Leu Leu Ser
            20                  25                  30

Ser Gln Val Thr Gln Glu Leu Arg Ala Leu Met Asp Glu Thr Met Lys
            35                  40                  45

Glu Leu Lys Ala Tyr Lys Ser Glu Leu Glu Glu Gln Leu Thr Ala Arg
    50                  55                  60

Leu Ser Lys Glu Leu Gln Ala Ala Gln Ala Arg Leu Gly Ala Asp Met
65                  70                  75                  80

Glu Asp Val Cys Gly Arg Leu Val Gln Tyr Arg Gly Glu Val Gln Ala
                85                  90                  95

Met Leu Gly Gln Ser Thr Glu Glu Leu Arg Val Arg Leu Ala Ser His
            100                 105                 110

Leu Arg Lys Leu Arg Lys Arg Leu Leu Arg Asp Ala Asp Asp Leu Gln
            115                 120                 125

Lys Arg Leu Ala Val Tyr Gln Ala
        130                 135

<210> SEQ ID NO 28
<211> LENGTH: 45
<212> TYPE: PRT
<213> ORGANISM: Artificial Sequence
<220> FEATURE:
<223> OTHER INFORMATION: COMP coiled-coil domain

<400> SEQUENCE: 28

Asp Leu Gly Pro Gln Met Leu Arg Glu Leu Gln Glu Thr Asn Ala Ala
1               5                   10                  15

Leu Gln Asp Val Arg Glu Leu Leu Arg Gln Gln Val Arg Glu Ile Thr
            20                  25                  30

Phe Leu Lys Asn Thr Val Met Glu Cys Asp Ala Cys Gly
```

35                  40                  45

<210> SEQ ID NO 29
<211> LENGTH: 24
<212> TYPE: PRT
<213> ORGANISM: Artificial Sequence
<220> FEATURE:
<223> OTHER INFORMATION: tyrp-1 transmembrane sequence

<400> SEQUENCE: 29

Ile Ile Ala Ile Ala Val Val Gly Ala Leu Leu Leu Val Ala Leu Ile
1               5                   10                  15

Phe Gly Thr Ala Ser Tyr Leu Ile
            20

<210> SEQ ID NO 30
<211> LENGTH: 40
<212> TYPE: PRT
<213> ORGANISM: Artificial Sequence
<220> FEATURE:
<223> OTHER INFORMATION: CD28 co-stimulatory endodomain

<400> SEQUENCE: 30

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 31
<211> LENGTH: 36
<212> TYPE: PRT
<213> ORGANISM: Artificial Sequence
<220> FEATURE:
<223> OTHER INFORMATION: OX40 endodomain

<400> SEQUENCE: 31

Arg Asp Gln Arg Leu Pro Pro Asp Ala His Lys Pro Pro Gly Gly Gly
1               5                   10                  15

Ser Phe Arg Thr Pro Ile Gln Glu Glu Gln Ala Asp Ala His Ser Thr
            20                  25                  30

Leu Ala Lys Ile
        35

<210> SEQ ID NO 32
<211> LENGTH: 42
<212> TYPE: PRT
<213> ORGANISM: Artificial Sequence
<220> FEATURE:
<223> OTHER INFORMATION: 4-1BB endodomain

<400> SEQUENCE: 32

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 33
<211> LENGTH: 112
<212> TYPE: PRT

```
<213> ORGANISM: Artificial Sequence
<220> FEATURE:
<223> OTHER INFORMATION: CD3zeta endodomain

<400> SEQUENCE: 33

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 34
<211> LENGTH: 20
<212> TYPE: PRT
<213> ORGANISM: Thosea asigna virus

<400> SEQUENCE: 34

Arg Ala Glu Gly Arg Gly Ser Leu Leu Thr Cys Gly Asp Val Glu Glu
1               5                   10                  15

Asn Pro Gly Pro
            20

<210> SEQ ID NO 35
<211> LENGTH: 5
<212> TYPE: PRT
<213> ORGANISM: Artificial Sequence
<220> FEATURE:
<223> OTHER INFORMATION: truncated COMP coiled-coil domain (5 C-terminal
      amino acids)

<400> SEQUENCE: 35

Cys Asp Ala Cys Gly
1               5

<210> SEQ ID NO 36
<211> LENGTH: 20
<212> TYPE: PRT
<213> ORGANISM: Artificial Sequence
<220> FEATURE:
<223> OTHER INFORMATION: truncated COMP coiled-coil domain (C-terminus)

<400> SEQUENCE: 36

Gln Gln Val Arg Glu Ile Thr Phe Leu Lys Asn Thr Val Met Glu Cys
1               5                   10                  15

Asp Ala Cys Gly
            20
```

CHIMERIC ANTIGEN RECEPTOR

FIELD OF THE INVENTION

The present invention relates to a chimeric antigen receptor (CAR) which specifically binds to the human CD22 antigen.

BACKGROUND TO THE INVENTION

Chimeric Antigen Receptors (CARs)

Chimeric antigen receptors are proteins which graft the specificity of, for example, a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1A).

The most common form of these molecules are fusions of single-chain variable fragments (scFv) derived from monoclonal antibodies which recognize a target antigen, fused via a spacer and a trans-membrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

CD22

The human CD22 antigen is a molecule belonging to the SIGLEC family of lectins. It is found on the surface of mature B cells and on some immature B cells and is expressed on 60-70% of neoplastic B cells.

CD22 is a sugar binding transmembrane protein, which specifically binds sialic acid with an immunoglobulin (Ig) domain located at its N-terminus. CD22 functions as an inhibitory receptor for B cell receptor (BCR) signalling.

Like CD19, CD22 is widely considered to be a pan-B antigen, although expression on some non-lymphoid tissue has been described. Targeting of CD22 with therapeutic monoclonal antibodies and immunoconjugates has entered clinical testing.

There have also been various reports of chimeric antigen receptors (CARs) targeting CD22. Haso et al. (Blood; 2013; 121(7)) describe anti-CD22 CARs with antigen-binding domains derived from m971, HA22 and BL22 scFvs.

CD-22 has seven extracellular IgG-like domains, which are commonly identified as Ig domain 1 to Ig domain 7, with Ig domain 7 being most proximal to the B cell membrane and Ig domain 7 being the most distal from the Ig cell membrane (see FIG. 2 and Haso et al 2013 as above FIG. 2B).

The large extracellular domain of CD22 is considered a challenge for CAR targeting. It is known that activation of canonical TCR chains is critically dependent on the size of the MHC ligand being recognised, with signalling attenuating sharply when the TCR:peptide-MHC ligand pair size exceeds wild-type dimensions (Choudhuri et al (2005) Nature 436:578-582). The mechanism underlying this phenomenon has been explained with reference to the kinetic segregation model of T cell activation. Extended length T cell:target cell interactions are thought to be incapable or inefficient at excluding the phosphatases CD45 and CD148 from the synapse, leading to inefficient phosphorylation of the TCR complex and inefficient signalling (Davis and van der Merwe (2006) Nat Immunol. 7: 803-809). It has also been shown that CARs exhibit diminished signalling efficiency as the distance of the epitope from the target cell membrane increases (Hombach et al (2007) J. Immunol. 178:4650-4657).

The seven Ig-like domains of CD22 provide a number of epitopes at varying distances from the membrane which can be targeted using distinct mAbs. In studies investigating the impact of CD22 epitope membrane proximity on CAR T-cell activation and target cell lysis it has been reported that there is an inverse relationship between maximum lytic potential and distance of the CD22 epitope from the target cell membrane (James et al. (2008) J. Immunol. 7028-7038). This is in complete correlation with the model mentioned above.

In the study by James et al (2008) it was found that, even when targeting a membrane-proximal epitope, CD22-specific CAR T cells exhibited lower levels of maximum lysis and lower antigen sensitivity that CAR T-cells targeting CD20, which has a shorter extracellular domain than CD22. This diminished sensitivity was restored by targeting a ligand expressing the same epitope, but constructed as a truncated CD22 molecule to approximate to the length of a TCR:peptide-MHC complex.

Haso et al (2013, as above) made and tested CARs with binding domains based on the anti-CD22 antibodies HA22, BL22 and m971. HA22 and BL22 scFvs bind to Ig domain 3 of CD22, whereas m971 binds within Ig domain 5-7 of CD22 which are proximal to the membrane (see FIG. 1 and Haso et al (2013) FIG. 2B). It was reported that the m971-derived CAR showed superior target cell killing activity than the HA22-derived CAR and the BL22-derived CAR, which finding is attributed to the importance of the CD22 epitope targeted by the CAR. It is concluded that targeting a membrane proximal domain of CD22 is "the key element" in developing a highly active anti-CD22 CAR (Discussion, last paragraph).

The m971-derived CAR is currently in clinical trial for the treatment of B-cell acute lymphoblastic leukemia (B-ALL).

A panel of CD22 CARs having different antigen binding domains were compared for their in vitro killing activity against Raji cells in a 4:1 and a 1:1 E:T ratio.

Figure 5:

FIG. 5: IFNγ release assay

The panel of CD22 CARs having different antigen binding domains were compared for IFNγ secretion after 72 h co-culture with Raji target cells at a 4:1 and a 1:1 E:T ratio.

SUMMARY OF ASPECTS OF THE INVENTION

The present inventors have developed a new anti-CD22 CAR which surprisingly outperforms other anti-CD22 CARs, targeting different epitopes of CD22, in target cell killing.

Thus, in a first aspect, the present invention provides a chimeric antigen receptor (CAR) which comprises a CD22-binding domain which comprises
a) a heavy chain variable region (VH) having complementarity determining regions (CDRs) with the following sequences:

```
                CDR1
                            (SEQ ID No. 1)
                NYWIH;

CDR2
                            (SEQ ID No. 2)
                GINPGNNYATYRRKFQG

CDR3
                            (SEQ ID No. 3)
                EGYGNYGAWFAY;
``` and
b) a light chain variable region (VL) having CDRs with the following sequences:

```
                CDR1
                            (SEQ ID No. 4)
                RSSQSLANSYGNTFLS;

CDR2
                            (SEQ ID No. 5)
                GISNRFS

CDR3
                            (SEQ ID No. 6)
                LQGTHQPYT.
```

The CD22-binding domain may comprise a VH domain having the sequence shown as SEQ ID No. 7; or a VL domain having the sequence shown as SEQ ID No 8 or a variant thereof having at least 90% sequence identity which retains the capacity to bind CD22.

The CAR may comprise a spacer domain selected from the following: a human an IgG1 Fc domain; an IgG1 hinge; an IgG1 hinge-CD8 stalk; a CD8 stalk; or a coiled-coil spacer domain. In particular, the CAR may comprise a coiled-coil spacer, which produces a multimeric CAR at the cell surface when expressed in a cell.

In a second aspect, the present invention provides a nucleic acid sequence which encodes a CAR according to the first aspect of the invention.

In a third aspect, there is provided a nucleic acid construct which comprises a first nucleic acid sequence according to the second aspect of the invention and a second nucleic acid sequence encoding another CAR or a suicide gene.

In a fourth aspect there is provided a vector which comprises a nucleic acid sequence according to the second aspect of the invention or a nucleic acid construct according to the third aspect of the invention.

In a fifth aspect there is provided a cell which expresses a CAR according to the first aspect of the invention.

In a sixth aspect, there is provided a method for making a cell according to the fifth aspect of the invention, which comprises the step of introducing a nucleic acid sequence according to the second aspect of the invention, or a nucleic acid construct according to the third aspect of the invention into a cell.

In a seventh aspect, there is provided a pharmaceutical composition which comprises a plurality of cells according to the fifth aspect of the invention.

In an eighth aspect there is provided a method for treating a disease which comprises the step of administering a pharmaceutical composition according to the seventh aspect of the invention to a subject.

There is also provided a pharmaceutical composition according to the seventh aspect of the invention for use in the treatment of a disease.

There is also provided a cell according to the fifth aspect of the invention for use in the preparation of a pharmaceutical composition for the treatment of a disease.

The disease may be a cancer, such as a B-cell malignancy.

DETAILED DESCRIPTION

Chimeric Antigen Receptors (CARs)

Figure 1:
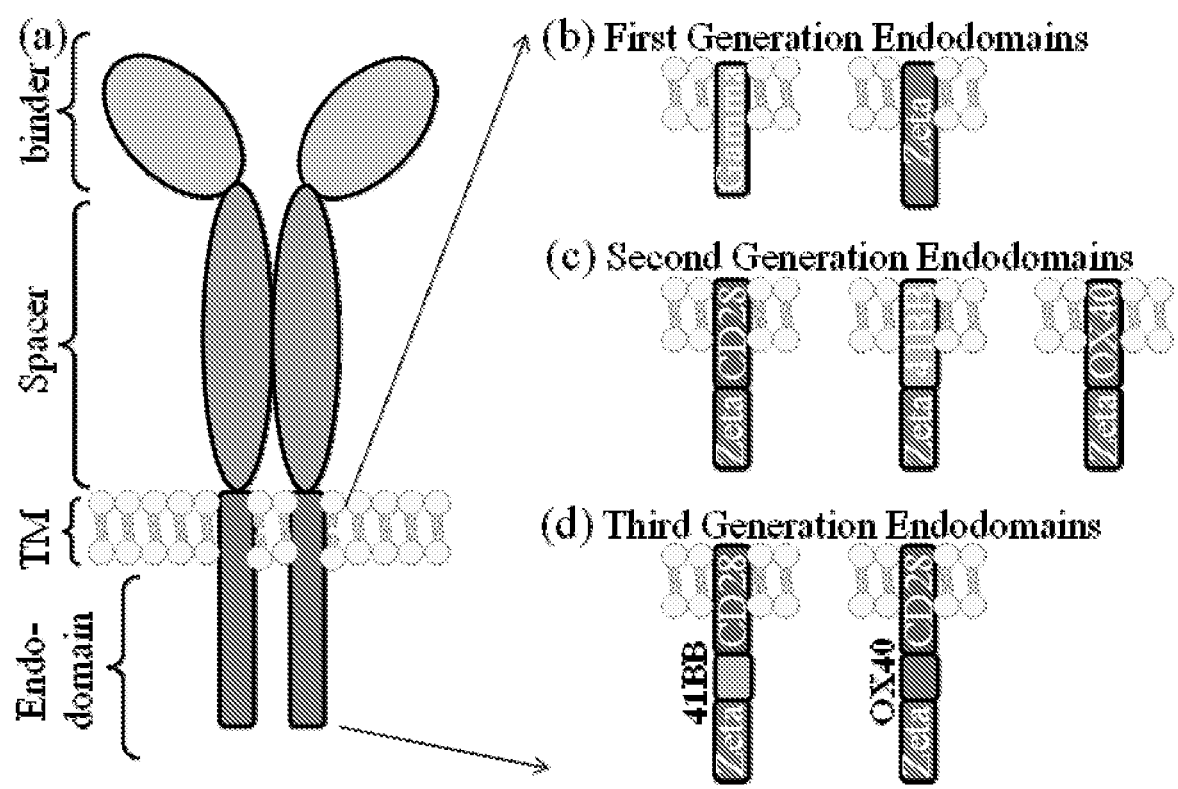
FIG. 1: a) Schematic diagram illustrating a classical CAR. (b) to (d): Different generations and permutations of CAR endodomains: (b) initial designs transmitted ITAM signals alone through FcεR1-γ or CD3ζ, endodomain, while later designs transmitted additional (c) one or (d) two co-stimulatory signals in the same compound endodomain.

CARs, which are shown schematically in FIG. 1, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8a and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ, results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. Lentiviral vectors may be employed. In this way, a large number of cancer-specific T cells can be generated for adoptive cell transfer. When the CAR binds the target-antigen, this results in the transmission of an activating signal to the T-cell it is expressed on. Thus the CAR directs the specificity and cytotoxicity of the T cell towards tumour cells expressing the targeted antigen.

Antigen Binding Domain

The antigen binding domain is the portion of the CAR which recognizes antigen. Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain antibody; an artificial single binder such as a Darpin (designed ankyrin repeat protein); or a single-chain derived from a T-cell receptor.

The antigen binding domain of the CAR of the present invention is derived from Inotuzumab, which has the following complementarity Determining Regions (CDRs):

```
Heavy chain:
CDR1
                              (SEQ ID No. 1)
NYWIH;

CDR2
                              (SEQ ID No. 2)
GINPGNNYATYRRKFQG

CDR3
                              (SEQ ID No. 3)
EGYGNYGAWFAY;
and

Light chain:
CDR1
                              (SEQ ID No. 4)
RSSQSLANSYGNTFLS;

CDR2
                              (SEQ ID No. 5)
GISNRFS

CDR3
                              (SEQ ID No. 6)
LQGTHQPYT.
```

The CAR of the present invention may have one or more mutations (substitutions, additions or deletions) in one or more the CDRs provided that the resultant molecule retains the capacity to bind CD22. For example, the or each CDR may comprise one, two or three mutations compared to the sequences given above. The mutations may be in CDR1 or 2, or the light chain CDRs, which are often less critical for antigen binding.

The CAR of the present invention may comprise the VH and/or VL from Inotuzumab, which are given below as SEQ ID Nos. 7 and 8 respectively. The CDR sequences are in bold and underlined and are based on the Kabat delineation system.

SEQ ID No. 7: VH sequence
EVQLVQSGAEVKKPGASVKVSCKASGYRFTNYWIHWVRQAPGQGLEWIG

GINPGNNYATYRRKFQGRVTMTADTSTSTVYMELSSLRSEDTAVYYCTRE

GYGNYGAWFAYWGQGTLVTVSS

SEQ ID No. 8: VL sequence
DVQVTQSPSSLSASVGDRVTITCRSSQSLANSYGNTFLSWYLHKPGKAP

QLLIYGISNRFSGVPDRFSGSGSGTDFTLTISSLQPEDFATYYCLQGTH

QPYTFGQGTKVEIK

The CAR of the invention may comprise a variant of the sequence shown as SEQ ID No. 7 and/or 8 having at least 80, 85, 90, 95, 98 or 99% sequence identity, provided that the variant sequence retain the capacity to bind CD22 (when in conjunction with a complementary VL or VH domain, if appropriate).

The percentage identity between two polypeptide sequences may be readily determined by programs such as BLAST which is freely available at http://blast.ncbl.nlm.nlh.gov.

The antigen binding domain of the CAR of the present invention may comprise an scFv, which may be in a VH-VL orientation or a VL-VH orientation.

Human CD22 is a single-pass type I transmembrane protein having 847 amino acids, of which residues 20-687 make up the N-terminal extracellular domain, residues 688-706 make up the transmembrane domain and residues 707-847 make up the C-terminal cytoplasmic domain.

The extracellular domain is made up of seven extracellular IgG-like domains, which are commonly identified as Ig domain 1 to Ig domain 7, with Ig domain 7 being most proximal to the B cell membrane and Ig domain 7 being the most distal from the Ig cell membrane (see Haso et al 2013 as above FIG. 2B).

The positions of the Ig domains in terms of the amino acid sequence of CD22 (http:www.uniprot.org/uniprot/P20273) are summarised in the following table:

| Ig domain | Amino acids |
|---|---|
| 1 | 20-138 |
| 2 | 143-235 |
| 3 | 242-326 |
| 4 | 331-416 |
| 5 | 419-500 |
| 6 | 505-582 |
| 7 | 593-676 |

The antigen-binding domain of the CAR of the present invention binds to an epitope on Ig domain 1 of CD22.

Signal Peptide

The CARs of the cell of the present invention may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the SEQ ID No. 9, 10 or 11 or a variant thereof having 5, 4, 3, 2 or 1 amino acid mutations (insertions, substitutions or additions) provided that the signal peptide still functions to cause cell surface expression of the CAR.

SEQ ID No. 9: MGTSLLCWMALCLLGADHADG

The signal peptide of SEQ ID No. 9 is compact and highly efficient. It is predicted to give about 95% cleavage after the terminal glycine, giving efficient removal by signal peptidase.

SEQ ID No. 10: MSLPVTALLLPLALLLHAARP

The signal peptide of SEQ ID No. 10 is derived from IgG1.

SEQ ID No. 11: MAVPTQVLGLLLLWLTDARC

The signal peptide of SEQ ID No. 11 is derived from CD8.

Spacer Domain

CARs may comprise a spacer sequence to connect the antigen-binding domain with the transmembrane domain and spatially separate the antigen-binding domain from the cell membrane. A flexible spacer allows the antigen-binding domain to orient in different directions to facilitate binding.

The CAR of the present invention may, for example, comprise a spacer derived from an IgG1 Fc region, an IgG1 hinge or the human or mouse CD8 stalk. A human IgG1 spacer may be altered to remove Fc binding motifs.

Amino acid sequences for these spacers are given below:

(hinge-CH2CH3 of human IgG1)
SEQ ID No. 12
AEPKSPDKTHTCPPCPAPPVAGPSVFLFPPKPKDTLMIARTPEVTCVVV

DVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGKKD (human CD8 stalk):
SEQ ID No. 13
TTTPAPRPPTPAPTIASQPLSLRPEACRPAAGGAVHTRGLDFACDI (human IgG1 hinge):
SEQ ID No. 14
AEPKSPDKTHTCPPCPKDPK Alternatively the CAR of the present invention may comprise a coiled-coil spacer domain.

A coiled coil is a structural motif in which two to seven alpha-helices are wrapped together like the strands of a rope. Many endogenous proteins incorporate coiled coil domains. The coiled coil domain may be involved in protein folding (e.g. it interacts with several alpha helical motifs within the same protein chain) or responsible for protein-protein interaction. In the latter case, the coiled coil can initiate homo or hetero oligomer structures.

The use of a coiled-coil spacer domain causes the CAR to multimerise at the cell surface, effectively increasing the local concentration of antigen-binding domains. This is particularly useful for targeting low density antigens. CD22 is present at a relatively low density on B cells, being detected at a copy number of about 30,000 molecules/cell compared to 100,000-150,000 molecules/cell of CD20.

The use of a coiled-coil spacer generates a hyper-sensitive CAR as the valency of the CAR is increased. The use of a coiled-coil spacer domain increases the number of ITAMs present and the avidity of the oligomeric CAR complex.

The structure of coiled coil domains is well known in the art. For example as described by Lupas & Gruber (Advances in Protein Chemistry; 2007; 70; 37-38).

Coiled coils usually contain a repeated pattern, hxxhcxc, of hydrophobic (h) and charged (c) amino-acid residues, referred to as a heptad repeat. The positions in the heptad repeat are usually labeled abcdefg, where a and d are the hydrophobic positions, often being occupied by isoleucine, leucine, or valine. Folding a sequence with this repeating pattern into an alpha-helical secondary structure causes the hydrophobic residues to be presented as a 'stripe' that coils gently around the helix in left-handed fashion, forming an amphipathic structure. The most favourable way for two such helices to arrange themselves in the cytoplasm is to wrap the hydrophobic strands against each other sandwiched between the hydrophilic amino acids. Thus, it is the burial of hydrophobic surfaces that provides the thermodynamic driving force for the oligomerization. The packing in a coiled-coil interface is exceptionally tight, with almost complete van der Waals contact between the side-chains of the a and d residues.

The α-helices may be parallel or anti-parallel, and usually adopt a left-handed super-coil. Although disfavoured, a few right-handed coiled coils have also been observed in nature and in designed proteins.

The coiled coil domain is capable of forming a coiled coil multimer such that a multimeric CAR complex is formed.

The relationship between the sequence and the final folded structure of a coiled coil domain are well understood in the art (Mahrenholz et al; Molecular & Cellular Proteomics; 2011; 10(5):M110.004994). As such the coiled coil domain may be a synthetically generated coiled coil domain.

Examples of proteins which contain a coiled coil domain include, but are not limited to, kinesin motor protein, hepatitis D delta antigen, archaeal box C/D sRNP core protein, cartilage-oligomeric matrix protein (COMP), mannose-binding protein A, coiled-coil serine-rich protein 1, polypeptide release factor 2, SNAP-25, SNARE, Lac repressor or apolipoprotein E.

The sequence of various coiled coil domains is shown below:

Kinesin motor protein: parallel homodimer (SEQ ID No. 15)

MHAALSTEVVHLRQRTEELLRCNEQQAAELETCKEQLFQSNMERKELH

NTVMDLRGN

Hepatitis D delta antigen: parallel homodimer (SEQ ID No. 16)

GREDILEQWVSGRKKLEELERDLRKLKKKIKKLEEDNPWLGNIKGIIGKY

Archaeal box C/D sRNP core protein: anti-parallel heterodimer (SEQ ID No. 17)

RYVVALVKALEEIDESINMLNEKLEDIRAVKESEITEKFEKKIRELREL

RRDVEREIEEVM

Mannose-binding protein A: parallel homotrimer (SEQ ID No. 18)

AIEVKLANMEAEINTLKSKLELTNKLHAFSM

Coiled-coil serine-rich protein 1: parallel homotrimer (SEQ ID No. 19)

EWEALEKKLAALESKLQALEKKLEALEHG

Polypeptide release factor 2: anti-parallel heterotrimer

Chain A:
(SEQ ID No. 20)
INPVNNRIQDLTERSDVLRGYLDY

Chain B:
(SEQ ID No. 21)
VVDTLDQMKQGLEDVSGLLELAVEADDEETFNEAVAELDALEEKLAQ

LEFR

SNAP-25 and SNARE: parallel heterotetramer

Chain A:
(SEQ ID No. 22)
IETRHSEIIKLENSIRELHDMFMDMAMLVESQGEMIDRIEYNVEHAVDY

VE

Chain B:
(SEQ ID No. 23)
ALSEIETRHSEIIKLENSIRELHDMFMDMAMLVESQGEMIDRIEYNVEH

AVDYVERAVSDTKKAVKY

Chain C:
(SEQ ID No. 24)
ELEEMQRRADQLADESLESTRRMLQLVEESKDAGIRTLVMLDEQGEQ

LERIEEGMDQINKDMKEAEKNL

Chain D:
(SEQ ID No. 25)
IETRHSEIIKLENSIRELHDMFMDMAMLVESQGEMIDRIEYNVEHAVDY

VE

Lac repressor: parallel homotetramer (SEQ ID No. 26)
SPRALADSLMQLARQVSRLE

Apolipoprotein E: anti-parallel heterotetramer (SEQ ID No. 27)
SGQRWELALGRFWDYLRWVQTLSEQVQEELLSSQVTQELRALMDETMKEL

KAYKSELEEQLTARLSKELQAAQARLGADMEDVCGRLVQYRGEVQAMLGQ

STEELRVRLASHLRKLRKRLLRDADDLQKRLAVYQA

The coiled coil domain is capable of multimerization. Depending on the sequence selected, the coiled coil domain may be capable of forming, for example a trimer, a tetramer, a pentamer, a hexamer or a heptamer.

The coiled coil domain may be the COMP coiled coil domain.

COMP is one of the most stable protein complexes in nature (stable from 0° C.–100° C. and a wide range of pH) and can only be denatured with 4-6M guanidine hydrochloride. The COMP coiled coil domain is capable of forming a pentamer. COMP is also an endogenously expressed protein that is naturally expressed in the extracellular space. This reduces the risk of immunogenicity compared to synthetic spacers. Furthermore, the crystal structure of the COMP coiled coil motif has been solved which gives an accurate estimation on the spacer length. The COMP structure is ~5.6 nm in length (compared to the hinge and CH2CH3 domains from human IgG which is ~8.1 nm).

The coiled coil domain may consist of or comprise the sequence shown as SEQ ID No. 28 or a fragment thereof.

(SEQ ID No. 28)
DLGPQMLRELQETNAALQDVRELLRQQVREITFLKNTVMECDACG

It is possible to truncate the COMP coiled-coil domain at the N-terminus and retain surface expression. The coiled-coil domain may therefore comprise or consist of a truncated version of SEQ ID No. 28, which is truncated at the N-terminus. The truncated COMP may comprise the 5 C-terminal amino acids of SEQ ID No. 28, i.e. the sequence CDACG (SEQ ID No. 35). The truncated COMP may comprise 5 to 44 amino acids, for example, at least 5, 10, 15, 20, 25, 30, 35 or 40 amino acids. The truncated COMP may correspond to the C-terminus of SEQ ID No. 28. For example a truncated COMP comprising 20 amino acids may comprise the sequences QQVREITFLKNTVMECDACG (SEQ ID No. 36). Truncated COMP may retain the cysteine residue(s) involved in multimerisation. Truncated COMP may retain the capacity to form multimers.

Various coiled coil domains are known which form hexamers such as gp41dervived from HIV, and an artificial protein designed hexamer coiled coil described by N. Zaccai et al. (2011) Nature Chem. Bio., (7) 935-941). A mutant form of the GCN4-p1 leucine zipper forms a heptameric coiled-coil structure (J. Liu. et al., (2006) PNAS (103) 15457-15462).

The coiled coil domain may comprise a variant of one of the coiled coil domains described above, providing that the variant sequence retains the capacity to form a coiled coil oligomer. For example, the coiled coil domain may comprise a variant of the sequence shown as SEQ ID No. 15 to 28 having at least 80, 85, 90, 95, 98 or 99% sequence identity, providing that the variant sequence retains the capacity to form a coiled coil oligomer.

Transmembrane Domain

The transmembrane domain is the sequence of the CAR that spans the membrane.

A transmembrane domain may be any protein structure which is thermodynamically stable in a membrane. This is typically an alpha helix comprising of several hydrophobic residues. The transmembrane domain of any transmembrane protein can be used to supply the transmembrane portion of the invention. The presence and span of a transmembrane domain of a protein can be determined by those skilled in the art using the TMHMM algorithm (http://www.cbs.dtu.dk/services/TMHMM-2.0/). Further, given that the transmembrane domain of a protein is a relatively simple structure, i.e a polypeptide sequence predicted to form a hydrophobic alpha helix of sufficient length to span the membrane, an artificially designed TM domain may also be used (U.S. Pat. No. 7,052,906 B1 describes synthetic transmembrane components).

The transmembrane domain may be derived from CD28, which gives good receptor stability.

The transmembrane domain may be derived from human Tyrp-1. The tyrp-1 transmembrane sequence is shown as SEQ ID No. 29.

(SEQ ID No. 29)
IIAIAVVGALLLVALIFGTASYLI

Endodomain

The CAR of the invention may comprise or associate with an activating endodomain, the signal-transmission portion of the CAR. After antigen recognition, receptors cluster, native CD45 and CD148 are excluded from the synapse and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

The endodomain may comprise:
(i) an ITAM-containing endodomain, such as the endodomain from CD3 zeta; and/or
(ii) a co-stimulatory domain, such as the endodomain from CD28; and/or
(iii) a domain which transmits a survival signal, for example a TNF receptor family endodomain such as OX-40 or 4-1BB.

An endodomain which contains an ITAM motif can act as an activation endodomain in this invention. Several proteins are known to contain endodomains with one or more ITAM motifs. Examples of such proteins include the CD3 epsilon chain, the CD3 gamma chain and the CD3 delta chain to name a few. The ITAM motif can be easily recognized as a tyrosine separated from a leucine or isoleucine by any two other amino acids, giving the signature YxxL/I. Typically, but not always, two of these motifs are separated by between 6 and 8 amino acids in the tail of the molecule (YxxL/Ix(6-8)YxxL/I). Hence, one skilled in the art can readily find existing proteins which contain one or more ITAM to transmit an activation signal. Further, given the motif is simple and a complex secondary structure is not required, one skilled in the art can design polypeptides containing artificial ITAMs to transmit an activation signal (see WO 2000/063372, which relates to synthetic signalling molecules).

The sequence of some endodomains and co-stimulatory domains are given below.

SEQ ID No. 30 (CD28 co-stimulatory endodomain)

SKRSRLLHSDYMNMTPRRPGPTRKHYQPYAPPRDFAAYRS

SEQ ID No. 31 (OX40 endodomain)

RDQRLPPDAHKPPGGGSFRTPIQEEQADAHSTLAKI

SEQ ID No. 32 (4-1BB endodomain)

KRGRKKLLYIFKQPFMRPVQTTQEEDGCSCRFPEEEEGGCEL

SEQ ID No. 33 (CD3zeta endodomain)

RVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR

The CAR of the invention may comprise a variant of any of the sequences shown as SEQ ID No. 30-33 having at least 80, 85, 90, 95, 98 or 99% sequence identity, provided that the variant sequence retains the capacity to induce T-cell signalling upon antigen recognition, i.e. provide the relevant activation/proliferation or survival signal to T cells.

Nucleic Acid Sequence

The second aspect of the invention relates to a nucleic acid sequence which encodes a CAR as defined in the first aspect of the invention.

The nucleic acid sequence may be, for example, an RNA, a DNA or a cDNA sequence.

The nucleic acid sequence may have the following structure:

AgB-spacer-TM or

AgB-spacer-TM-endo in which

AgB is a nucleic acid sequence encoding the antigen-binding domain;
spacer is a nucleic acid sequence encoding the spacer; and
TM is a nucleic acid sequence encoding the transmembrane domain.

Nucleic Acid Construct

The present invention also provides a nucleic acid construct which comprises at least two nucleic acid sequences: a first nucleic acid sequence encoding a CAR of the invention; and a second nucleic acid sequence encoding, for example, a second CAR or a suicide gene.

The second CAR may bind CD19.

The nucleic acid may produce a polypeptide which comprises the two CAR molecules (or CAR and suicide gene) joined by a cleavage site. The cleavage site may be self-cleaving, such that when the polypeptide is produced, it is immediately cleaved into the first and second CARs without the need for any external cleavage activity.

Various self-cleaving sites are known, including the Foot-and-Mouth disease virus (FMDV) 2A peptide and similar sequence (Donnelly et al, Journal of General Virology (2001), 82, 1027-1041), for instance like the 2A-like sequence from Thosea asigna virus which has the sequence shown as SEQ ID No. 34:

SEQ ID No. 34
RAEGRGSLLTCGDVEENPGP.

The co-expressing sequence may be an internal ribosome entry sequence (IRES).

The co-expressing sequence may be an internal promoter.

Where the nucleic acid construct encodes two CARs, it may have the following structure:

AgB1-spacer1-TM1-coexpr-AbB2-spacer2-TM2 in which

AgB1 is a nucleic acid sequence encoding the antigen-binding domain of a first CAR;
spacer 1 is a nucleic acid sequence encoding the spacer of a first CAR;
TM1 is a nucleic acid sequence encoding the transmembrane domain of a first CAR;
coexpr is a nucleic acid sequence enabling co-expression of both CARs
AgB2 is a nucleic acid sequence encoding the antigen-binding domain of a second CAR;
spacer 2 is a nucleic acid sequence encoding the spacer of a second CAR;
TM2 is a nucleic acid sequence encoding the transmembrane domain of a second CAR;
which nucleic acid sequence, when expressed in a cell, encodes a polypeptide which is cleaved at the cleavage site such that the first and second CARs are co-expressed at the cell surface.

One or both CARs may also comprise an endodomain. Where both CARs comprise an endodomain the nucleic acid construct may have the structure:

AgB1-spacer1-TM1-endo1-coexpr-AbB2-spacer2-TM2-endo2

Alternative codons may be used in regions of sequence encoding the same or similar amino acid sequences, in order to avoid homologous recombination.

Suicide genes encode polypeptide which are capable of causing apoptosis of the cell on which they are expressed under certain condition. For example, the sort-suicide gene RQR8 described in WO2013/153391 causes apoptosis of the cell in the presence of rituximab.

Vector

The present invention also provides a vector, or kit of vectors which comprises one or more CAR-encoding nucleic acid sequence(s). Such a vector may be used to introduce the nucleic acid sequence into a host cell so that it expresses the CAR of the invention.

The vector may, for example, be a plasmid or a viral vector, such as a retroviral vector or a lentiviral vector, or a transposon based vector or synthetic mRNA.

The vector may be capable of transfecting or transducing a cell such as a T cell.

Cell

The present invention relates to a cell which comprises a CAR of the present invention.

The cell may be any eukaryotic cell capable of expressing a CAR at the cell surface, such as an immunological cell.

In particular the cell may be an immune effector cell such as a T cell or a natural killer (NK) cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytotoxic T cells (TC cells, or CTLs) destroy virally infected cells and tumour cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell of the invention may be any of the T cell types mentioned above, in particular a CTL.

Natural killer (NK) cells are a type of cytolytic cell which forms part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

CAR-expressing cells, such as CAR-expressing T or NK cells may either be created ex vivo either from a patient's own peripheral blood (1st party), or in the setting of a haematopoietic stem cell transplant from donor peripheral blood (2nd party), or peripheral blood from an unconnected donor (3rd party).

The present invention also provide a cell composition comprising CAR expressing cells according to the present invention. The cell composition may be made by transducing a blood-sample ex vivo with a nucleic acid according to the present invention.

Alternatively, CAR-expressing cells may be derived from ex vivo differentiation of inducible progenitor cells or embryonic progenitor cells to the relevant cell type, such as T cells. Alternatively, an immortalized cell line such as a T-cell line which retains its lytic function and could act as a therapeutic may be used.

In all these embodiments, CAR cells are generated by introducing DNA or RNA coding for the CARs by one of many means including transduction with a viral vector, transfection with DNA or RNA.

A CAR T cell of the invention may be an ex vivo T cell from a subject. The T cell may be from a peripheral blood mononuclear cell (PBMC) sample. T cells may be activated and/or expanded prior to being transduced with CAR-encoding nucleic acid, for example by treatment with an anti-CD3 monoclonal antibody.

A CAR T cell of the invention may be made by:
(i) isolation of a T cell-containing sample from a subject or other sources listed above; and
(ii) transduction or transfection of the T cells with one or more nucleic acid sequence(s) encoding the first and second CAR.

The T cells may then by purified, for example, selected on the basis of co-expression of the first and second CAR.

Pharmaceutical Composition

The present invention also relates to a pharmaceutical composition containing a plurality of CAR-expressing cells, such as T cells or NK cells according to the first aspect of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The cells of the present invention are capable of killing cancer cells, such as B-cell lymphoma cells. CAR-expressing cells, such as T cells, may either be created ex vivo either from a patient's own peripheral blood (1st party), or in the setting of a haematopoietic stem cell transplant from donor peripheral blood (2nd party), or peripheral blood from an unconnected donor (3rd party). Alternatively, CAR T-cells may be derived from ex-vivo differentiation of inducible progenitor cells or embryonic progenitor cells to T-cells. In these instances, CAR T-cells are generated by introducing DNA or RNA coding for the CAR by one of many means including transduction with a viral vector, transfection with DNA or RNA.

The cells of the present invention may be capable of killing target cells, such as cancer cells. The target cell is recognisable by expression of CD22.

TABLE 4 expression of lymphoid antigens on lymphoid leukaemias

| | CD19 | CD22 | CD10 | CD7 | CD5 | CD3 | clg μ | slg μ |
|---|---|---|---|---|---|---|---|---|
| Early pre-B | 100 | >95 | 95 | 5 | 0 | 0 | 0 | 0 |
| Pre-B | 100 | 100 | >95 | 0 | 0 | 0 | 100 | 0 |
| Transitional pre-B | 100 | 100 | 50 | 0 | 0 | 0 | 100 | 0 |
| B | 100 | 100 | 50 | 0 | 0 | 0 | >95 | >95 |
| T | <5 | 0 | 0 | 100 | 95 | 100 | 0 | 0 |

Taken from Campana et al. (Immunophenotyping of leukemia. J. Immunol. Methods 243, 59-75 (2000)). clg μ—cytoplasic Immunoglobulin heavy chain; slg μ—surface Immunoglobulin heavy chain.

Figure 2:
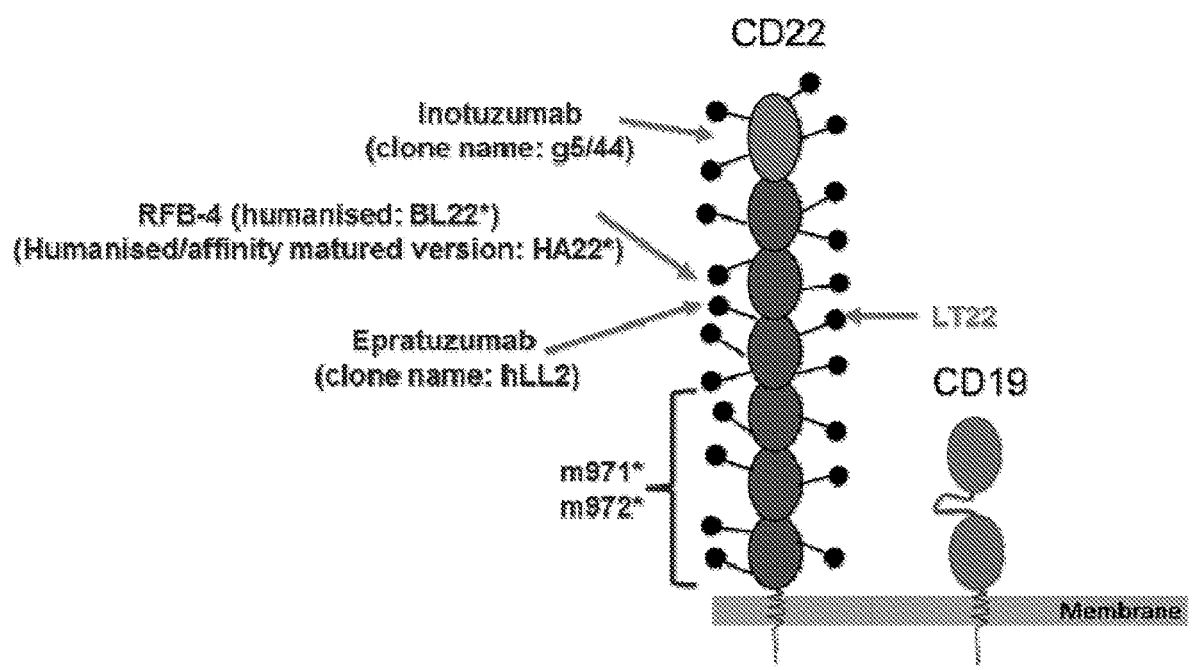
FIG. 2: Schematic diagram illustrating the 7 Ig-like domains of CD22 and the binding position of various anti-CD22 antibodies. CD19, by comparison, has a much smaller, more flexible, extracellular domain, comprising two Ig-like domains.

The expression of commonly studied lymphoid antigens on different types of B-cell leukaemias closely mirrors that of B-cell ontogeny (see FIG. 2).

The cells of the present invention may be used to treat cancer, in particular B-cell malignancies.

Examples of cancers which express CD22 are B-cell lymphomas, including Hodgkin's lymphoma and non-Hodgkins lymphoma; and B-cell leukaemias.

For example the B-cell lymphoma may be Diffuse large B cell lymphoma (DLBCL), Follicular lymphoma, Marginal zone lymphoma (MZL) or Mucosa-Associated Lymphatic Tissue lymphoma (MALT), Small cell lymphocytic lymphoma (overlaps with Chronic lymphocytic leukemia), Mantle cell lymphoma (MCL), Burkitt lymphoma, Primary mediastinal (thymic) large B-cell lymphoma, Lymphoplasmacytic lymphoma (may manifest as Waldenstrom macroglobulinemia), Nodal marginal zone B cell lymphoma (NMZL), Splenic marginal zone lymphoma (SMZL), Intravascular large B-cell lymphoma, Primary effusion lymphoma, Lymphomatoid granulomatosis, T cell/histiocyte-rich large B-cell lymphoma or Primary central nervous system lymphoma.

The B-cell leukaemia may be acute lymphoblastic leukaemia, B-cell chronic lymphocytic leukaemia, B-cell prolymphocytic leukaemia, precursor B lymphoblastic leukaemia or hairy cell leukaemia.

The B-cell leukaemia may be acute lymphoblastic leukaemia.

Treatment with the cells of the invention may help prevent the escape or release of tumour cells which often occurs with standard approaches.

The invention will now be further described by way of Examples, which are meant to serve to assist one of ordinary skill in the art in carrying out the invention and are not intended in any way to limit the scope of the invention.

EXAMPLES

Example 1—Comparative Functional Assays with Anti-CD22 CARs

A panel of CARs were created comprising binding domains derived from various different anti-CD22 antibodies, and their function was compared.

The CAR comprising an scFv based on M971 can be considered as the gold standard as this CAR is in clinical development.

Figure 3:
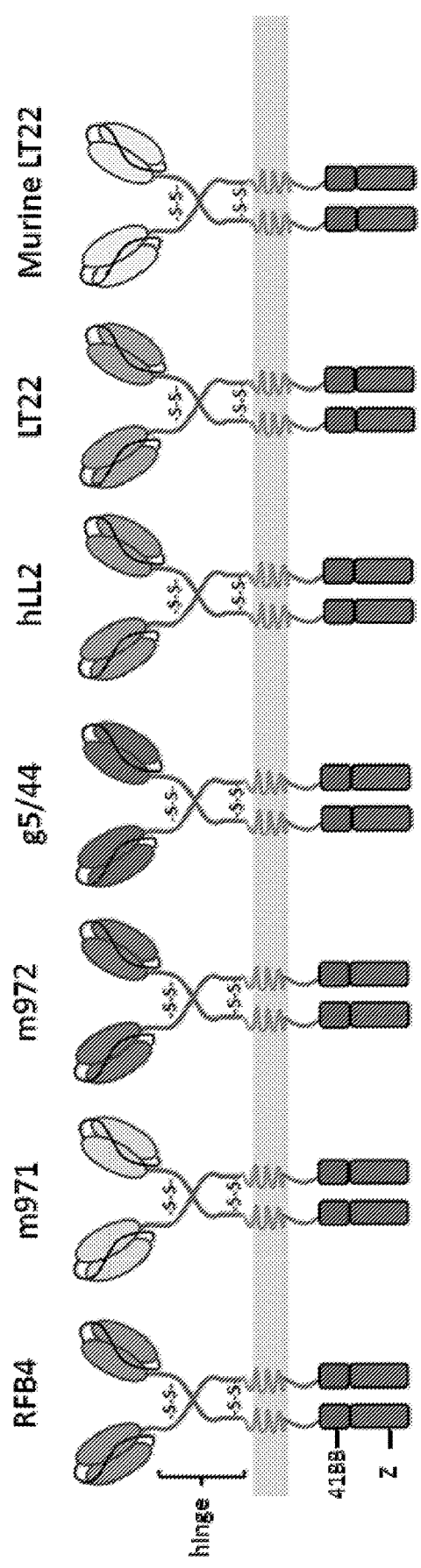
FIG. 3: Schematic diagram illustrating the seven different anti-CD22 CARs tested in the Examples. The CARs were identical except for the antigen binding domains, each having an IgG1 hinge spacer, and a second generation endodomain comprising CD3 zeta and a 41BB co-stimulatory domain.

CARs were constructed and expressed based on the mAbs RFB4, m971, m972, g5/44, hLL2, LT22 and murine LT22. Their structure is shown in FIG. 3. The CARs differed solely in their antigen binding domain. In all constructs, the binding domains were linked to the membrane with a IgG1 hinge spacer and contained intracellular activatory motifs from 41BB and CD3-zeta.

Retroviruses were produced by transient transfection of 293T cells with plasmids encoding the CARs, gag/pol and the envelope protein RD114. After 3 days the supernatants were harvested and used to transduce PHA/IL2-activated PBMCs with equal titres of retrovirus on retronectin-coated plates. Six days post-transduction CAR-expression was confirmed by flow cytometry and PBMCs were co-cultured in a 1:1 and a 4:1 E:T ratio with Raji target cells. Target cell killing was assayed after 72 hours co-culture. Supernatants were removed and interferon-γ levels were assayed by ELISA.

Figure 4:
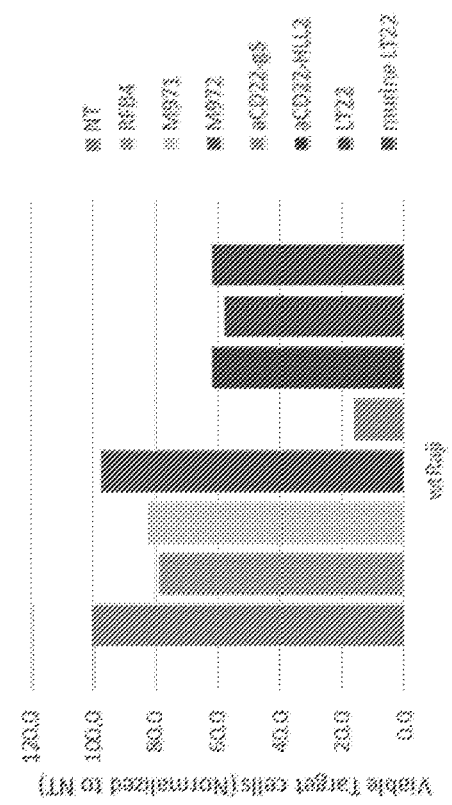
FIG. 4: Cytotoxicity assay
Figure 4:
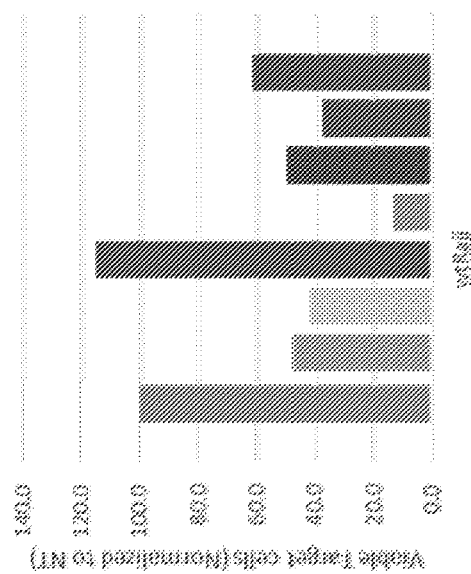

The results are shown in FIGS. 4 and 5.

The CAR having a g5/44 binding domain showed the best killing activity at both a 4:1 and 1:1 E:T ratio (FIG. 4). The CAR having a g5/44 binding domain also showed maximal interferon gamma release after 72 hours co-culture at both a 4:1 and 1:1 E:T ratio (FIG. 5).

As discussed in the Background section above, there is a widely accepted understanding in the field that a) T cell activation is critically dependent on the combined length of the TCR/CAR and antigen at the T-cell target-cell synapse; b) CD22 is inherently difficult to target with a CAR because it has such a long extracellular domain, and c) it is critical to target a membrane-proximal epitope of CD22 in order to obtain satisfactory killing activity (Haso et al (2013, as above); James et al (2008 as above); and Long et al (2013, Oncolmmunology 2:4 e23621).

James et al (2008, as above) describe a study in which two anti-CD22 CARs are compared: one which has an antigen binding domain based on HD39, which binds the most membrane distal Ig domain 1 of CD22, and one which has an antigen binding domain based on RFB4 which binds the more membrane proximal Ig domain 3 of CD22 (James et al 2008, FIG. 1B). It was found that the RBF4 based CAR produced a higher level of maximal lysis than the HD39 based CAR, which was attributed to the differences in distance between the target antigen epitopes.

Haso et al (2013, as above) describe a study in which three anti-CD22 CARs are compared: one which has an antigen binding domain based on HA22, which binds Ig domain 3 of CD22; one which has an antigen binding domain based on BL22, which also binds Ig domain 3 of CD22; and one which has an antigen binding domain based on m971, which binds the more membrane proximal Ig domain 5-7 of CD22. The m971-derived CAR showed superior target cell killing activity than either of the CARs which bind Ig domain 3 of CD22. This finding tallied with the earlier results of James et al and seemingly confirmed that targeting a membrane proximal domain of CD22 is critical in developing an effective anti-CD22 CAR.

The results shown here in FIGS. 4 and 5 are therefore particularly surprising, as g5/44 binds to the extreme N-terminal Ig domain 1 of CD22 which is the most membrane distal epitope of CD22 for all the CARs tested. As shown in FIG. 2, hLL2, LT22 and RFB4 all bind to Ig domain 3 and m971 and m972 bind to Ig domains 5-7 of CD22. It would be expected from the findings of James et al (2008, as above), Haso et al (2013, as above) and the previously accepted underlying molecular mechanism, that the CARs binding Ig domains 5-7 would give the best killing activity, followed by the CARs which bind Ig domain 3, and that the CAR which binds Ig domain 1 would give the worst killing activity. By contrast the CAR based on g5/44 outperformed all the CARs which bind to more membrane proximal epitopes.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, oncology or related fields are intended to be within the scope of the following claims.

The invention claimed is:

1. A chimeric antigen receptor (CAR) which comprises a CD22-binding single-chain variable fragment (scFv) domain which comprises
   a) a heavy chain variable region (VH) having complementarity determining regions (CDRs) with the following sequences:

CDR1
                                    (SEQ ID No. 1)
    NYWIH;

CDR2
                                    (SEQ ID No. 2)
    GINPGNNYATYRRKFQG

CDR3
                                    (SEQ ID No. 3)
    EGYGNYGAWFAY;

and
   b) a light chain variable region (VL) having CDRs with the following sequences:

CDR1
                                    (SEQ ID No. 4)
    RSSQSLANSYGNTFLS;

CDR2
                                    (SEQ ID No. 5)
    GISNRFS

CDR3
                                    (SEQ ID No. 6)
    LQGTHQPYT.

2. A CAR according to claim 1, wherein the CD22-binding domain comprises a VH domain having the sequence shown as SEQ ID No. 7; or a VL domain having the sequence shown as SEQ ID No 8 or a variant thereof having at least 90% sequence identity which retains the capacity to bind CD22.

3. A CAR according to claim 1, which comprises a spacer domain selected from the following: a human IgG1 Fc domain; an IgG1 hinge; an IgG1 hinge-CD8 stalk; a CD8 stalk; or a coiled-coil spacer domain.

4. A nucleic acid sequence which encodes a CAR according to claim 1.

5. A nucleic acid construct which comprises a first nucleic acid sequence according to claim 4 and a second nucleic acid sequence encoding another CAR or a suicide gene.

6. A vector which comprises a nucleic acid sequence according to claim 4.

7. A vector which comprises a nucleic acid construct according to claim 5.

8. A cell which expresses a CAR according to claim 1.

9. A method for making a cell according to claim 8, which comprises the step of introducing into a cell a nucleic acid sequence which encodes a chimeric antigen receptor (CAR) which comprises a CD22-binding single-chain variable fragment (scFv) domain which comprises
   a) a heavy chain variable region (VH) having complementarity determining regions (CDRs) with the following sequences:

CDR1 - NYWIH              (SEQ ID No. 1);
    CDR2 - GINPGNNYATYRRKFQG  (SEQ ID No. 2)
    CDR3 - EGYGNYGAWFAY       (SEQ ID No. 3);

and
   b) a light chain variable region (VL) having CDRs with the following sequences:

CDR1 - RSSQSLANSYGNTFLS   (SEQ ID No. 4);
    CDR2 - GISNRFS            (SEQ ID No. 5)
    CDR3 - LQGTHQPYT          (SEQ ID No. 6).

10. A pharmaceutical composition which comprises a plurality of cells according to claim 8.

11. A method for treating a B-cell malignancy which comprises the step of administering a pharmaceutical composition according to claim 10 to a subject.

12. A method for making a cell according to claim 8, which comprises the step of introducing into a cell a nucleic acid construct which encodes a chimeric antigen receptor (CAR) which comprises a CD22-binding single-chain variable fragment (scFv) domain which comprises
   a) a heavy chain variable region (VH) having complementarity determining regions (CDRs) with the following sequences:

CDR1 - NYWIH;             (SEQ ID No. 1);
    CDR2 - GINPGNNYATYRRKFQG  (SEQ ID No. 2)
    CDR3 - EGYGNYGAWFAY;      (SEQ ID No. 3);

and
   b) a light chain variable region (VL) having CDRs with the following sequences:

CDR1 - RSSQSLANSYGNTFLS   (SEQ ID No. 4);
    CDR2 - GISNRFS            (SEQ ID No. 5)
    CDR3 - LQGTHQPYT          (SEQ ID No. 6).

* * * * *

UNITED STATES PATENT AND TRADEMARK OFFICE
CERTIFICATE OF CORRECTION

PATENT NO. : 11,180,553 B2
APPLICATION NO. : 16/310121
DATED : November 23, 2021
INVENTOR(S) : Shimobi Onuoha et al.

It is certified that error appears in the above-identified patent and that said Letters Patent is hereby corrected as shown below:

In the Claims

At Column 37, Line 4, "comprises" should be -- comprises: --.

At Column 37, Lines 10-19, "
```
        CDR1
                                (SEQ ID No. 1)
        NYWIH;

CDR2
                                (SEQ ID No. 2)
        GINPGNNYATYRRKFQG

CDR3
                                (SEQ ID No. 3)
        EGYGNYGAWFAY;
```
" should be
```
-- CDR1 - NYWIH              (SEQ ID No. 1);
   CDR2 - GINPGNNYATYRRKFQG  (SEQ ID No. 2)
   CDR3 - EGYGNYGAWFAY       (SEQ ID No. 3);--.
```

At Column 37, Lines 24-33, "
```
        CDR1
                                (SEQ ID No. 1)
        NYWIH;

CDR2
                                (SEQ ID No. 2)
        GINPGNNYATYRRKFQG

CDR3
                                (SEQ ID No. 3)
        EGYGNYGAWFAY;
```
" should be Signed and Sealed this
Twenty-seventh Day of September, 2022

*Katherine Kelly Vidal*

Katherine Kelly Vidal
*Director of the United States Patent and Trademark Office*

```
CDR1 - NYWIH              (SEQ ID No. 1);
CDR2 - GINPGNNYATYRRKFQG  (SEQ ID No. 2)
CDR3 - EGYGNYGAWFAY       (SEQ ID No. 3);--.
```

At Column 37, Line 37, "SEQ ID No 8" should be -- SEQ ID No. 8 --.

At Column 38, Line 8, "comprises" should be -- comprises: --.

At Column 38, Line 39, "CDR1 - NYWIH;" should be -- CDR1 - NYWIH --.

At Column 38, Line 41, "CDR3 - EGYGNYGAWFAY;" should be
-- CDR3 - EGYGNYGAWFAY --.